United States Patent [19]
Hart

[11] Patent Number: 5,976,111
[45] Date of Patent: Nov. 2, 1999

[54] AUTOMATICALLY POSITIONED HYPODERMIC NEEDLE GUARD

[75] Inventor: Kathleen S. Hart, Glencoe, Ill.

[73] Assignee: Emily A. Hart, Woodside, Calif.

[21] Appl. No.: 08/610,048

[22] Filed: Mar. 4, 1996

[51] Int. Cl.$^6$ .................................................. A61M 5/32
[52] U.S. Cl. ......................... 604/198; 604/110; 128/919
[58] Field of Search ................................... 604/192, 198, 604/263, 110, 195; 128/919

[56] References Cited

U.S. PATENT DOCUMENTS

| | | | |
|---|---|---|---|
| 4,917,101 | 4/1990 | Horn | 128/763 |
| 5,254,099 | 10/1993 | Kuracina et al. | 604/198 |
| 5,261,894 | 11/1993 | Smith et al. | 604/198 |
| 5,304,137 | 4/1994 | Fluke | 604/198 |
| 5,304,151 | 4/1994 | Kuracina | 604/198 |
| 5,336,187 | 8/1994 | Terry et al. | 604/198 |
| 5,336,200 | 8/1994 | Streck et al. | 604/198 |
| 5,417,660 | 5/1995 | Martin | 604/198 |
| 5,486,164 | 1/1996 | Streck | 604/198 |
| 5,492,536 | 2/1996 | Mascia | 604/198 |
| 5,662,610 | 9/1997 | Sircom | 604/198 |
| 5,688,241 | 11/1997 | Asbaghi | 604/198 |

*Primary Examiner*—Ronald Stright
*Attorney, Agent, or Firm*—Lumen Intellectual Property Services

[57] ABSTRACT

The invention presents an automatically positioned needle guard for a hypodermic needle. The needle guard includes a hollow stem having one end adapted to fit a syringe and an opposite end designed to hold the base of a hypodermic needle. One end of a housing is slidably mounted on the stem for sliding between a first position wherein the housing covers the needle and a second position wherein the needle tip protrudes from the housing. An elastic member is attached to the side of the stem, and a slidable ring is mounted around the stem near the elastic member. When expanded, the elastic member blocks the housing from sliding from the first position to second position. When the ring is slid over the elastic member, the ring forces the elastic member flush against the stem so that the housing can slide to its second position. After the needle has been used, a spring cooperative between the housing and stem automatically pushes the housing toward its first position. Upon exiting the housing, the elastic member expands to lock the housing in its first position covering the needle.

12 Claims, 7 Drawing Sheets

AUTOMATICALLY POSITIONED HYPODERMIC NEEDLE GUARD

BACKGROUND

1. Field of the Invention

The present invention relates to the field of safety devices for hypodermic needles, and in particular to an automatically positioned protective needle guard for a hypodermic needle.

2. Description of Prior Art

The hypodermic needle is one of the most useful tools in modern medicine, but it is also one of the most dangerous. In the urgent environment of ambulances or hospital emergency rooms, a hypodermic needle may accidentally stick a medical worker or patient. These accidental needle stick injuries are the main cause of occupationally acquired Hepatitis B, HIV, and other infections.

The most dangerous time in using a hypodermic needle is immediately before and after performing an injection, when the tip of the needle is usually exposed. At these times, an accidental drop or mis-handling of the needle by the operator could easily cause an accidental stick if the needle is not protected. Thus, there is a need for a needle guard that prevents the needle from being exposed before, during, and after the needle's use. Additionally, the needle guard should automatically re-position itself over the needle, since the operator will not be able to manually position the needle guard during an accidental drop or slip.

There have been numerous attempts to provide needle guards that perform these functions. Most of them involve an elastic element connected to a cover that encases the needle. For example, U.S. Pat. No. 5,256,152 issued to Marks on Mar. 11, 1992 describes a safety needle having a protective sheath for encasing the needle. The sheath has flexible ribs and a cup having an opening mis-aligned with the needle. A force applied to the cup bows the ribs and aligns the needle with the opening, so that the needle tip may pass through the opening into a patient's body.

This simple solution proposed by Marks has several disadvantages. First, it requires a person to handle the tip of the sheath to expose the needle, possibly leading to accidental punctures of the skin. Second, it provides no locking mechanism for keeping the needle encased once it has been used, so that an accidental stick may still occur when the needle is dropped or mis-handled. Third, the sheath is not strong enough to prevent the needle from jabbing through it.

More complex solutions have tried to address each of these problems. U.S. Pat. No. 5,242,401 issued to Colsky on Oct. 9, 1992 describes a protective needle head assembly. The assembly has a hub portion which attaches to a syringe and a cover portion for covering the needle head. The cover slides on a recessed, W-shaped track to expose the needle during use. After use, a spring automatically pushes the cover back along the track to a position covering the needle. This invention has the advantage of not requiring any extra effort to lock the needle in the exposed and covered positions, but its main disadvantage is that it is complicated to build, requiring precise machining for the track.

Another solution involving a needle cover that is guided on a track is described in U.S. Pat. No. 5,292,314 issued to D'Alessio et al. on Feb. 11, 1993. In this device, the needle cover has change-over slots to enable it to change directions when sliding on the track. A spring forces the cover back to its position protecting the needle after the needle is used. This device also has the advantage of locking the cover in a position that protects the needle. Unfortunately, it also has the disadvantage of requiring the user to manually rotate the cover after injection to initiate the return of the cover to the position in which the needle is protected. This manual step between needle exposure and needle covering does not prevent accidental sticks from occurring when the needle is dropped or mis-handled. This device also requires precise machining of the slots, which adds expense to its construction.

A simpler solution involving a manual locking mechanism is described in U.S. Pat. No. 5,246,428 issued to Falknor on Jul. 30, 1992. This device has a sheath that slides between a first position covering the needle and a second position exposing the needle for use. The sheath includes a latching mechanism which can lock the sheath into either position. A spring mounted within the sheath forces the sheath from its second position exposing the needle to its first position covering the needle after the latching mechanism has been manually released by an operator. This invention also suffers from the problem of requiring a manual step between exposing the needle for use and safely covering the needle after use. It is also difficult to produce a latch small enough to fit a sheath for a hypodermic needle, yet strong enough to resist breaking under pressure.

Another assembly having a spring loaded shield and latching mechanism for the shield is described in U.S. Pat. No. 4,863,435 issued to Sturman et al. on Aug. 24, 1988. In this assembly, the shield also moves between a first position covering the needle and a second position exposing the needle for use. However, the latching mechanism is only able to lock the shield in the second position that exposes the needle. After using the needle, the operator manually unlocks the latching mechanism, and the spring forces the shield back to its needle covering position. This invention suffers from the same disadvantage of requiring the operator to manually unlock the latching mechanism before the shield returns to its needle covering position. Additionally, this device has the disadvantage of not allowing the shield to be locked in a position that covers the needle.

Another device for protecting a needle is described in U.S. Pat. No. 5,336,187 issued to Terry et al. on Jun. 24, 1993. In this device, a syringe has a sleeve with a protective sheath for covering the needle of the syringe. A collapsible bellows is mounted inside the sleeve so that the bellows constantly urges the sheath toward a position that covers the needle. During use of the syringe, the pressure exerted on the sleeve by contact with a patient's body causes the sheath to retract so that the needle may be inserted into the body. As the needle is withdrawn from the body, the collapsed bellows expands, causing the sheath to automatically reposition itself in a protective position over the needle. The main disadvantage of this device is that it lacks a mechanism for locking the sheath in a position that covers the needle, so that an accidental pressure applied to the sleeve would also expose the needle, allowing an accidental stick. Additionally, this device must be attached permanently to the syringe, so that the device is not reusable.

Thus, no existing needle guard combines adequate safety features to prevent an accidental needle stick before, during, and after use of the needle. Additionally, no existing needle guard combines these features in a device that is simple to construct, inexpensive to manufacture, and easy to use.

OBJECTS AND ADVANTAGES OF THE INVENTION

In view of the above, it is an object of the present invention to provide a needle guard that prevents a hypodermic needle from accidentally sticking a patient or medical worker before, during, and after use of the needle. It is another object of the invention to provide a needle guard that is automatically locked in a position covering the needle before and after the needle is used for injection. It is a further object of the invention to provide a needle guard that can be unlocked for injection without requiring the user to manually manipulate the needle cover. It is another object of the invention to provide a needle guard having a needle cover that automatically moves and locks into a position covering the needle as the needle is withdrawn from injection.

It is anther object of the invention to provide a needle guard that includes a user-controllable over-ride feature so that the needle may be temporarily exposed for precise placement of the needle tip or for loading multiple medications into a syringe through the needle. It is a further object of the invention to provide a hypodermic needle guard with all of the above features that is simple to construct, inexpensive to manufacture, and easy to use.

These and other objects and advantages will become more apparent after consideration of the ensuing description and the accompanying drawings.

SUMMARY OF THE INVENTION

The invention provides an automatically positioned needle guard for a hypodermic needle. The needle guard includes a stem having a proximal end, a distal end, and an axial opening extending through the full length of the stem. The proximal end has flanged protrusions designed to screw into a threaded collar of a fluid port, such as an end of a syringe or catheter tube. The distal end has a needle fitting for attaching the hypodermic needle to the stem so that the hypodermic needle is in fluid flow communication with the fluid port through the axial opening.

The distal end of the stem is inserted into a housing having a collar end and an injection end. The collar end of the housing is slidably mounted on the stem, allowing the housing to slide on the stem between a first position wherein the housing covers the hypodermic needle and a second position wherein the needle partially protrudes from the injection end. A resilient member, such as a spring, is lodged between the housing and the stem for biasing the housing towards its first position, covering the needle. Thus, the resilient member automatically moves the housing into a position covering the needle.

An elastic member, such as a leaf spring, has a base attached to the exterior of the stem. The elastic member also has a spring body that tends to extend radially from the exterior of the stem. The elastic member prevents the housing from sliding from its first position to its second position when its body is radially extended from the stem. The elastic member permits the housing to slide from its first position to its second position when its body is flush with the stem.

A slidable retaining ring is fitted around the stem. The ring maintains the body of the elastic member flush with the stem when the ring is located at the distal end. The ring allows the body of the elastic member to extend radially from the stem when the ring is located at the proximal end. Thus, the housing can be locked in its first position covering the needle or unlocked to slide to its second position by sliding the ring.

In an alternative embodiment of the invention, the housing has a mounted end fixably mounted on the stem and a collar end for receiving a needle cover. The needle cover has an insertion end and an injection end. The insertion end is inserted into the housing through the collar. The collar end slidably grasps the needle cover to allow the needle cover to slide within the housing between a first position wherein the needle cover covers the needle and a second position wherein the needle partially protrudes from the injection end of the needle cover. A resilient member, such as a spring, is cooperative between the needle cover and the housing to bias the needle cover toward its first position, covering the needle.

In this embodiment, the elastic member and slidable retaining ring are mounted on the needle cover rather than on the stem. The elastic member prevents the needle cover from sliding from its first position to its second position when the body of the elastic member is radially extended from the needle cover and allows the needle cover to slide to its second position when the body is flush with the needle cover. The ring maintains the body flush with the needle cover when located at the insertion end and allows the body to extend radially from the needle cover when located at the injection end. Thus, the needle cover can be locked in its first position, covering the needle, or unlocked to slide to its second position for injecting the needle.

DETAILED DESCRIPTION OF THE INVENTION

Figure 1:
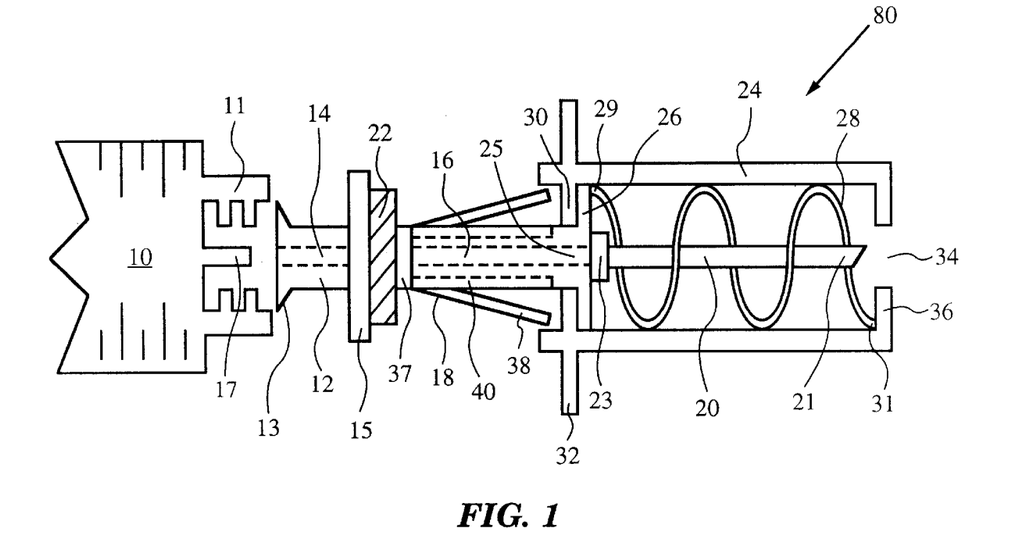
FIG. 1 is a schematic view of a needle guard locked in a position covering a needle.
Figure 2:
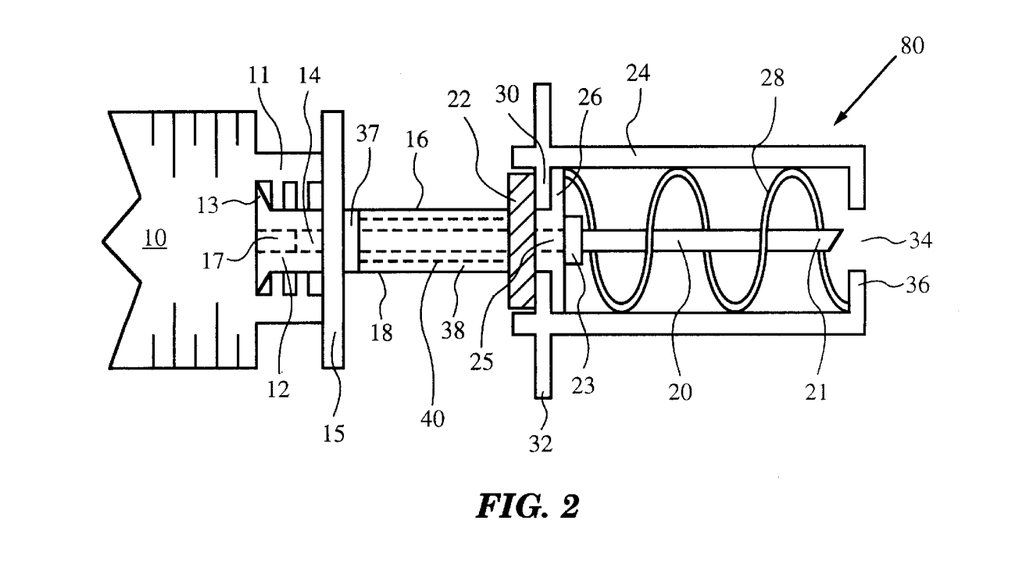
FIG. 2 is a schematic view of the needle guard of FIG. 1 in an unlocked position.
Figure 3:
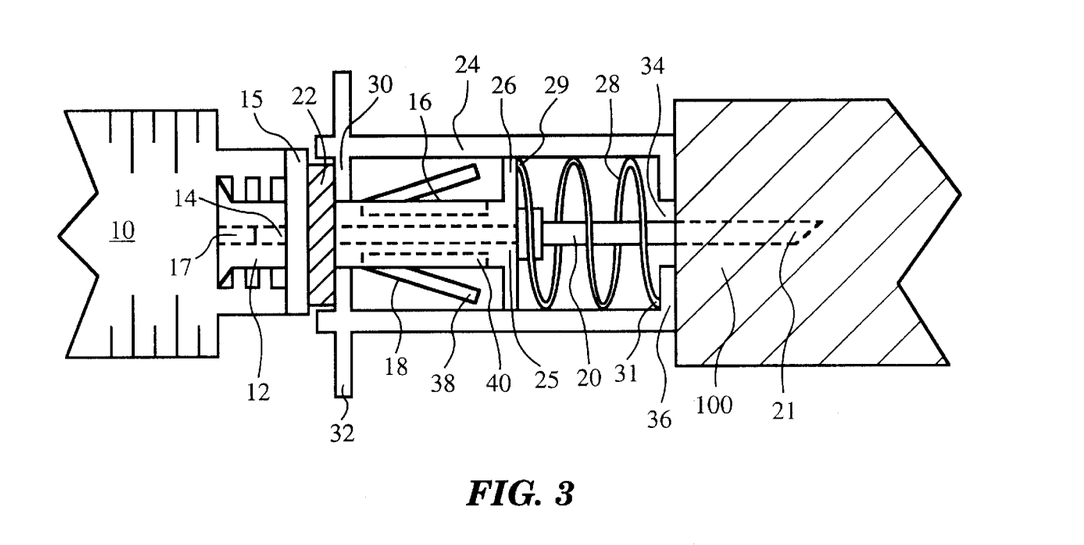
FIG. 3 is a schematic view of the needle guard of FIG. 1 during injection.

The preferred embodiment of the invention is illustrated in FIGS. 1–3. Referring to FIG. 1, a needle guard assembly 80 has a cylindrical stem 16 having a proximal end 12, a distal end 25, and an axial opening 14 extending the full length of stem 16. Proximal end 12 has two flanged protrusions 13 designed to screw into a threaded collar 11 of a syringe 10. Axial opening 14 is designed to receive a fluid port 17 of syringe 10 when flanged protrusions 13 are screwed into threaded collar 11, such that axial opening 14 is in fluid flow communication with fluid port 17. Specific techniques of attaching a stem to a syringe in this manner are well known in the art. Distal end 25 of stem 16 has a needle fitting 23 designed to receive a base of a needle 20. Needle 20 is mounted in fitting 23 in a manner well known in the art, such that needle 20 is in fluid flow communication with fluid port 17 through axial opening 14.

A cylindrical housing 24 has a collar end 30. Collar end 30 is slidably mounted on stem 16 at distal end 25. Within housing 24, distal end 25 terminates in a flange 26 that extends radially from the exterior of stem 16. Flange 26 has a diameter larger than the inner diameter of collar end 30. Collar end 30 is slidably mounted on stem 16 over flange 26 such that flange 26 prevents collar end 30 from sliding off distal end 25. Housing 24 has a length sufficient to cover the full length of needle 20 when collar end 30 is located at distal end 25. Opposite collar end 30, housing 24 has an injection end 36 shape in the form of a wall having a hole 34. Hole 34 is aligned with needle 20 and sufficiently large to allow a tip 21 of needle 20 to protrude through hole 34 when housing 24 slides towards proximal end 12 of stem 16.

A resilient member 28 is positioned within housing 24 for biasing housing 24 toward the position in which housing 24 fully covers needle 20. Resilient member 28 has a first end 29 pressing against flange 26 and a second end 31 pressing against injection end 36. In the preferred embodiment, resilient member 28 is a coiled helical spring that encircles needle 20. Resilient member 28 has a diameter sufficiently large to ensure that it does not contact needle 20 as it compresses and decompresses within housing 24. In the preferred embodiment, member 28 has a diameter equal to the inner diameter of housing 24. Attached to the outside of housing 24 are two finger handles 32 for facilitating the sliding of housing 24 toward proximal end 12 of stem 16.

Figure 14:
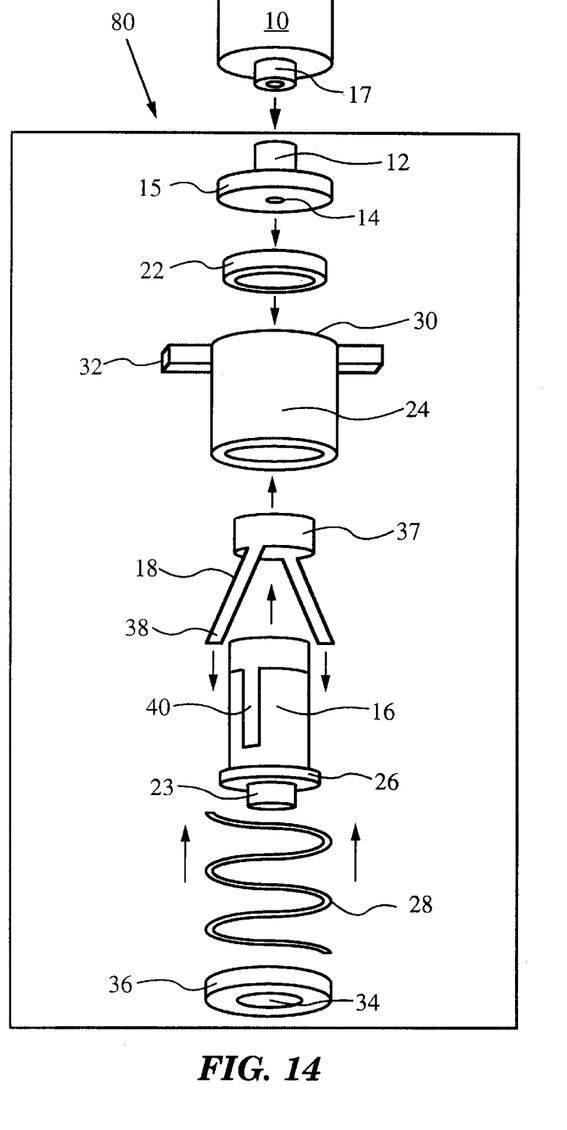
FIG. 14 is an exploded view illustrating the assembly of the needle guard of FIG. 1.

Two elastic members 18 have a common base 37 attached to the exterior of stem 16 between proximal end 12 and distal end 25. In this embodiment, members 18 are two leaf spring s having a ring-shaped base 37 mounted around stem 16, as shown in FIG. 14. Referring again to FIG. 1, members 18 each have a body 38 that tends to extend radially from the exterior of stem 16. This ensures that bodies 38 block the movement of housing 24 on stem 16 when they are extended to prevent housing 24 from sliding on stem 16 toward proximal end 12. Further, bodies 38 have a length sufficient to prevent housing 24 from sliding from distal end 25 when bodies 38 are radially extended from stem 16. Stem 16 has two slots 40 for receiving bodies 38 when bodies 38 are pressed flush with stem 16. Slots 40 are of the same size and shape as bodies 38 and are located on the exterior of stem 16 such that bodies 38 fit exactly into slots 40 when bodies 38 are pressed flush with stem 16.

A slidable retaining ring 22 is slidably mounted around stem 16 where base 37 is attached to stem 16. Ring 22 fits tightly around stem 16 so that ring 22 does not slide on stem 16 without the application of force. Ring 22 has an outer diameter larger than the inner diameter of collar end 30 to prevent ring 22 from entering housing 24. A flanged stop 15 extends radially from the exterior of proximal end 12 of stem 16. Stop 15 is for preventing ring 22 from sliding off proximal end 12. Stop 15 is located a sufficient distance from protrusions 13 to ensure that it does not interfere with the attachment of proximal end 12 to syringe 10. In the preferred embodiment, stop 15 has a diameter larger than the outer diameter of ring 22. This is to protect ring 22 from receiving an accidental force during a drop or mishandling of assembly 80. In alternative embodiments, stop 15 may have a diameter equal to or smaller than the outer diameter of ring 22.

The operation of the preferred embodiment is illustrated in FIGS. 1–3. Referring to FIG. 1, collar end 30 of housing 24 rests at distal end 25 of stem 16. In this safety position, housing 24 fully covers needle 20 and tip 21 to prevent tip 21 from accidentally sticking anybody. Bodies 38 of elastic members 18 are radially extended from stem 16 so that they block housing 24 from sliding from distal end 25, even if an accidental force were applied to injection end 36 of housing 24. Assembly 80 is stored in this locked safety position until a user wishes to perform an injection.

To perform an injection, the user first attaches proximal end 12 of stem 16 to syringe 10 by screwing protrusions 13 into threaded collar 11, as shown in FIG. 2. When protrusions 13 are screwed into threaded collar 11, needle 20 is in fluid flow communication with fluid port 17 through stem 16. Of course, assembly 80 may be attached to syringe 10 before storage, so that the first step of attaching assembly 80 to syringe 10 is already completed.

Referring to FIG. 2, the user slides ring 22 towards distal end 25 of stem 16. When ring 22 slides towards distal end 25, it pushes bodies 38 of members 18 into slots 40 so that bodies 38 become flush with stem 16. Referring to FIG. 3, the user then places injection end 36 of housing 24 against an injection object 100. Injection object 100 is an object requiring injection, such as the body of a patient, a vial of medicine, or any other object requiring injection. The user then pushes syringe 10 in the direction of injection end 36 while injection end 36 is contacting object 100. The force of contact between injection end 36 and injection object 100 causes housing 24 to slide on stem 16 toward stop 15. As housing 24 slides to this injection position, tip 21 protrudes from hole 34, entering injection object 100. Meanwhile, stem 16 advances further into housing 24, compressing resilient member 28 between flange 26 and injection end 36. Also, collar end 30 pushes ring 22 along stem 16 to stop 15.

To withdraw needle 20 from injection object 100, the user stops pushing syringe 10 towards injection end 36, so that there is no longer a force compressing resilient member 28. Member 28 then decompresses, exerting oppositely directed forces on flange 26 and injection end 36. The force applied on injection end 36 is in the direction of object 100, ensuring that injection end 36 remains in contact with object 100 during withdrawal of tip 21. This ensures that tip 21 is not exposed at any time during withdrawal. The force applied on flange 26 is in the direction of proximal end 12, pushing stem 16 out of housing 24 until flange 26 contacts collar end 30. As stem 16 is pushed out of housing 24 by member 28, housing 24 slides on stem 16 back to its safety position at distal end 25, thereby recovering needle 20 back into housing 24, as shown in FIG. 1.

As housing 24 slides back to distal end 25, ring 22 remains at stop 15 since there is no force on ring 22. As stem 16 slides out of housing 24, bodies 38 also slide out of collar end 30. Once bodies 38 are outside of collar end 30, they extend radially from stem 16, automatically locking assembly 80 to the safety position illustrated in FIG. 1. Housing 24 can slide on stem 16 again only after the user deliberately pushes ring 22 towards distal end 25 to bring bodies 38 flush with stem 16.

The advantage of needle guard assembly 80 described in this preferred embodiment is that needle 20 and tip 21 are not exposed at any time before, during or after the injection. Additionally, resilient member 28 automatically repositions housing 24 in a position covering needle 20 and tip 21 as soon as tip 21 is withdrawn from injected object 100, whether or not the withdrawal was intentional. No manual actions are required from the user to reposition housing 24, so that needle guard assembly 80 protects people in the event of an accidental drop or mishandling. Further, elastic members 18 automatically lock housing 24 in a position covering needle 20 and tip 21 so that an accidental force applied to injection end 36 will still not result in an accidental stick by tip 21.

Although constantly covering needle 20 is a highly desirable feature, the user may want to expose tip 21 for a brief period of time to facilitate exact placement of tip 21 on injection object 100. To temporarily expose tip 21, the user first slides ring 22 towards distal end 25 to force bodies 38 flush with stem 16. Next the user pulls handles 32 in the direction of proximal end 12 to slide housing 24 towards proximal end 12. As housing 24 slides, stem 16 advances further into housing 24 so that tip 21 protrudes from hole 34. The user now precisely places tip 21 on injection object 100 and release handles 32 to resume the operation of assembly 80 described above.

Figure 4:
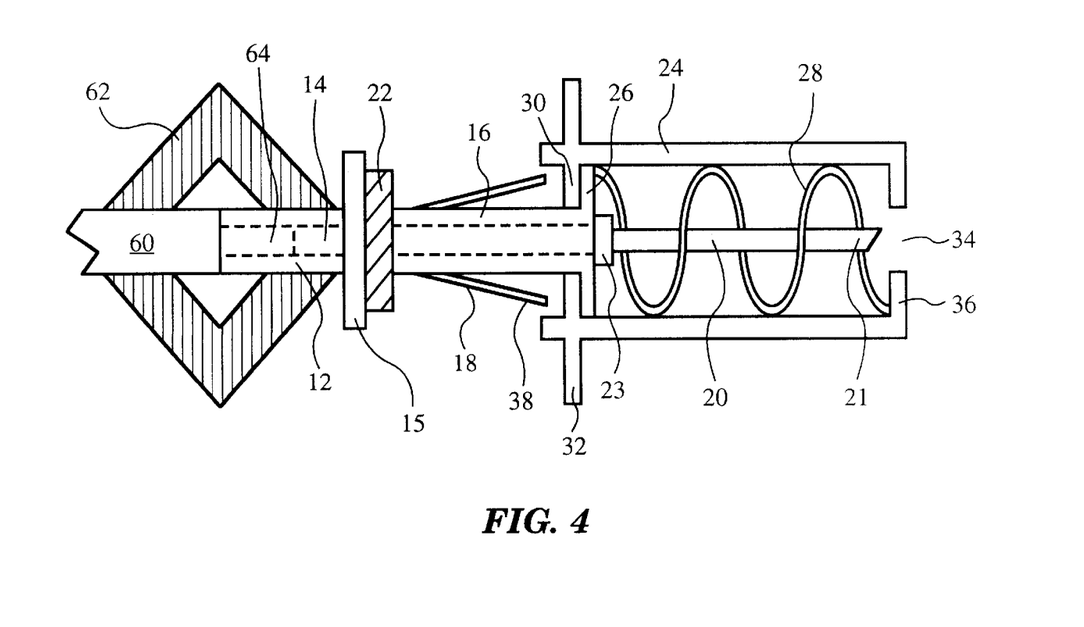
FIG. 4 is a schematic view of another needle guard according to the invention attached to a catheter tube.

A second embodiment of the invention is shown in FIG. 4. In this embodiment, proximal end 12 is adapted for attachment to a catheter tube 60 rather than syringe 10. Axial opening 14 is sized to receive a fluid port 64 located at the end of catheter tube 60. Two catheter clamps 62 clamp proximal end 12 to catheter tube 60 in a manner well known in the art. Other than attaching proximal end 12 to catheter tube 60 rather than syringe 10, the operation and advantages of this embodiment are identical to the operation and advantages of the preferred embodiment described above.

Figure 5:
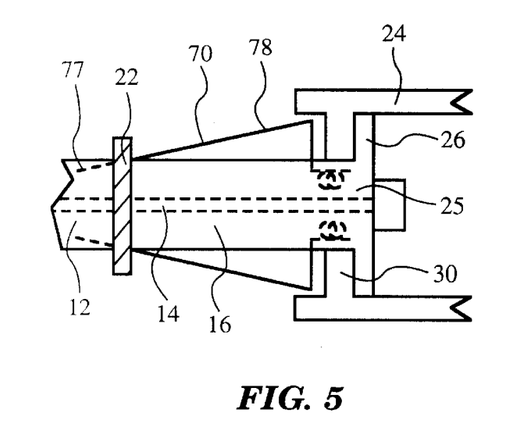
FIG. 5 is a schematic view of an alternative embodiment of the invention using L-springs.
Figure 6:
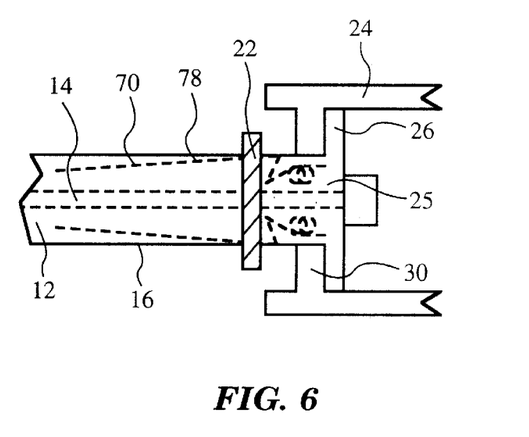
FIG. 6 is a schematic view of the L-springs of FIG. 5 being compressed.

A third embodiment of the invention is shown in FIG. 5 and FIG. 6. In this embodiment, the elastic members attached to stem 16 are L-springs instead of leaf springs. Like the leaf springs described in the preferred embodiment, two L-springs 70 each have a base 77 attached to stem 16 and a body 78 radially extended from stem 16, as shown in FIG. 5. When radially extended, bodies 78 prevent housing 24 from sliding from distal end 25. When ring 22 slides over L-springs 70, bodies 78 are pressed flush with stem 16, permitting housing 24 to slide on stem 16, as shown in FIG. 6. The main advantage of this third embodiment is that L-springs are less expensive than leaf springs and are often less complicated to attach to stem 16. Otherwise, the operation and advantages of this embodiment are identical to the operation and advantages of the preferred embodiment described above.

Figure 7:
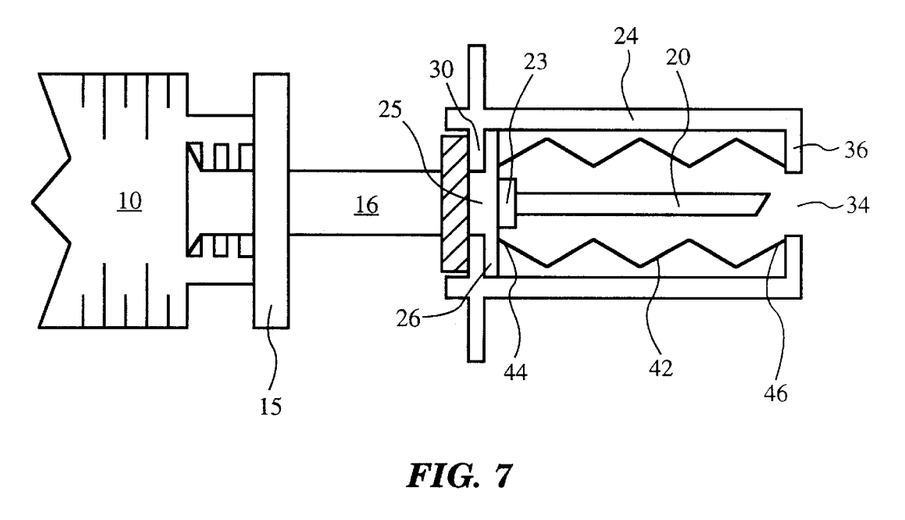
FIG. 7 is a schematic view of another needle guard according to the invention.

A fourth embodiment in which the resilient member is a collapsible bellows 42 instead of a helical spring is shown in FIG. 7. Like the helical spring of the preferred embodiment, bellows 42 has a first end 44 pressing against flange 26 and a second end 46 pressing against injection end 36. Bellows 42 is preferably made of plastic, similar to the bellows of a flexible drinking straw. Since plastic is often less expensive than metal, this embodiment has an economic advantage. Also, a plastic bellows is easier to attach than a helical spring, making this embodiment easier to manufacture. Other than using bellows 42 as the resilient member rather than a helical spring, the operation and advantages of this embodiment are identical to the operation and advantages of the preferred embodiment described above.

Figure 8:
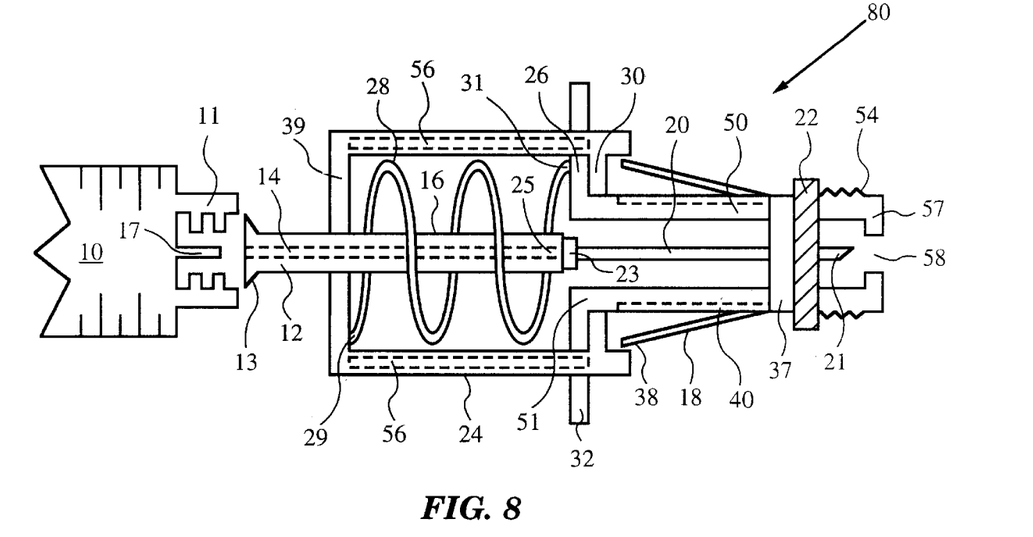
FIG. 8 is a schematic view of another needle guard locked in a position covering a needle.
Figure 9:
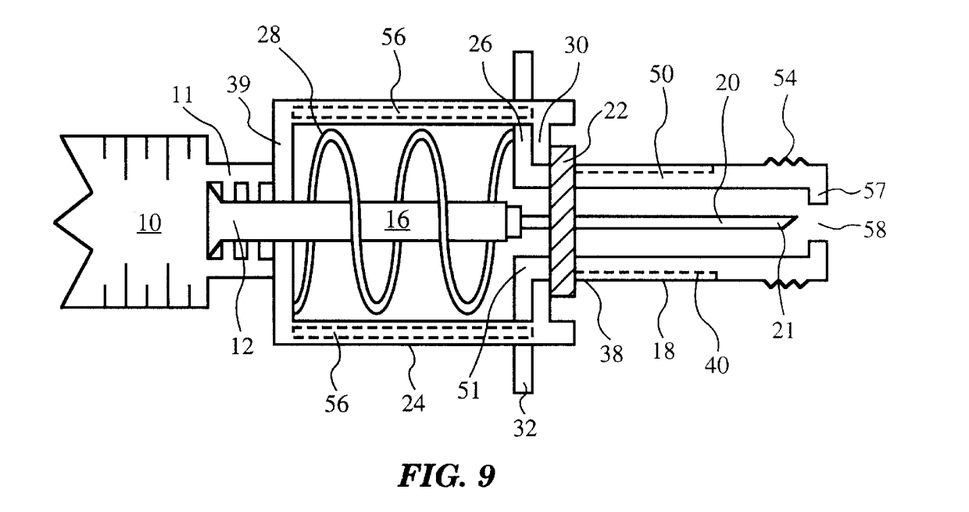
FIG. 9 is a schematic view of the needle guard of FIG. 8 in an unlocked position.
Figure 10:
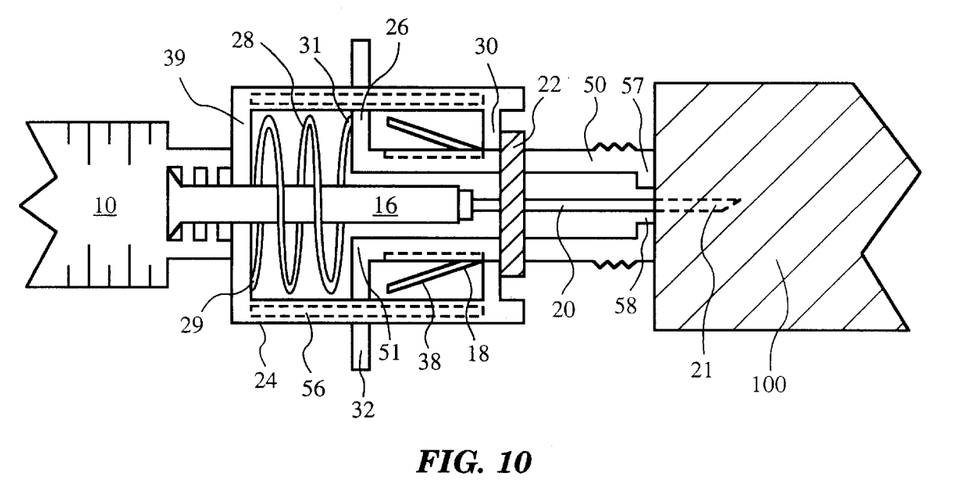
FIG. 10 is a schematic view of the needle guard of FIG. 8 during injection.

A fifth embodiment of the invention is shown in FIGS. 8–10. The primary difference in the fifth embodiment from the preferred embodiment is that housing 24 remains in a fixed position on stem 16, while a needle cover 50 slides within housing 24. Referring to FIG. 8, stem 16 is adapted at proximal end 12 to fit fluid port 17 and adapted at distal end 25 to accept needle 20 in fitting 23 in the same manner as described in the preferred embodiment above. However, unlike the preferred embodiment, housing 24 now has a mounted end 39 fixably mounted around stem 16 at proximal end 12. Mounted end 39 is mounted a sufficient distance from flanged protrusions 13 to ensure that housing 24 does not interfere with the attachment of proximal end 12 to fluid port 17.

Opposite mounted end 39, housing 24 has collar end 30. An insertion end 51 of needle cover 50 is inserted into collar end 30. Collar end 30 slidably grasps cover 50 to allow cover 50 to slide within housing 24. Within housing 24, insertion end 51 ends in flange 26. Flange 26 has a diameter larger than the inner diameter of collar end 30 so that flange 26 prevents insertion end 51 from sliding out of collar end 30. Cover 50 has a length sufficient to cover the full length of needle 20 when insertion end 51 is located at collar end 30. Opposite insertion end 51, cover 50 has an injection end 57 having a hole 58. Hole 58 is aligned with needle 20 and sufficiently large to allow tip 21 of needle 20 to protrude through hole 58 when cover 50 slides into housing 24.

A resilient member 28 is positioned within housing 24 for biasing cover 50 toward the position in which cover 50 fully covers needle 20. Resilient member 28 has a first end 29 pressing against mounted end 39 of housing 24 and a second end 31 pressing against injection end 57 of cover 50. In this embodiment, resilient member 28 is a coiled helical spring that encircles the portion of stem 16 within housing 24. Member 28 has a diameter sufficiently large to ensure that member 28 does not contact stem 16 as member 28 compresses and decompresses within housing 24.

Two lateral slots 56 are cut through opposite sides of housing 24. Slots 56 extend the length of housing 24 between mounted end 39 and collar end 30. Two finger handles 32 are attached to opposite sides of the exterior of insertion end 51 of cover 50. Handles 32 extend radially from insertion end 51 through slots 56. Handles 32 are for facilitating the sliding of cover 50 toward mounted end 39 of housing 24.

Two elastic members 18 have a base 37 attached to the exterior of cover 50 between injection end 57 and insertion end 51. In this embodiment, members 18 are two leaf springs having a ring-shaped base 37 mounted around stem 16. Members 18 each have a body 38 that tends to extend radially from the exterior of cover 50. This ensure that bodies 38 prevent cover 50 from sliding into housing 24 when they are extended. Further, bodies 38 have a length sufficient to prevent cover 50 from sliding from collar end 30 when bodies 38 are radially extended from cover 50. Cover 50 has two slots 40 for receiving bodies 38 when bodies 38 are pressed flush with cover 50. Slots 40 are of the same size and shape as bodies 38 and are located on the exterior of cover 50 such that bodies 38 fit exactly into slots 40 when bodies 38 are pressed flush with cover 50.

A slidable retaining ring 22 is slidably mounted around cover 50 where base 37 is attached to cover 50. Ring 22 fits tightly around the exterior of cover 50 so that ring 22 does not slide on cover 50 without the application of force. Ring 22 has an outer diameter larger than the inner diameter of collar end 30 to prevent ring 22 from entering housing 24. The exterior of cover 50 at injection end 57 has three ridges 54 designed to fit threaded grooves (not shown) on the inner surface of ring 22. Ridges 54 allow ring 22 to be screwed onto injection end 57 and prevent ring 22 from sliding off injection end 57.

The operation of the fifth embodiment is illustrated in FIGS. 8–10. The operation of the fifth embodiment differs from the operation of the preferred embodiment in that housing 24 remains fixed on stem 16 while cover 50 slides within housing 24. Referring to FIG. 8, insertion end 51 of cover 50 is located at collar end 30 of housing 24. In this safety position, cover 50 fully covers needle 20 and tip 21 to prevent tip 21 from accidentally sticking anybody. Bodies 38 of elastic members 18 are radially extended from the exterior of cover 50 so that they prevent cover 50 from sliding from collar end 30, even when an accidental force is applied to injection end 57. Assembly 80 is stored in this locked safety position until a user wishes to perform an injection.

Referring to FIG. 9, the user performs an injection by first sliding ring 22 towards insertion end 51 of cover 50. When ring 22 slides towards insertion end 51, it pushes bodies 38 of members 18 into slots 40 so that bodies 38 become flush with the exterior of cover 50. Referring to FIG. 10, the user then places injection end 57 against injection object 100 and pushes syringe 10 in the direction of injection end 57. The force of contact between injection end 57 and object 100 causes cover 50 to slide into housing 24 toward mounted end 39. As cover 50 slides to this injection position, tip 21 protrudes from hole 58, penetrating object 100. Meanwhile, resilient member 28 compresses between flange 26 and mounted end 39. Also, collar end 30 pushes ring 22 along cover 50 toward injection end 57.

To withdraw tip 21 from injection object 100, the user stops pushing syringe 10 towards injection end 57, so that there is no longer a force compressing resilient member 28. Member 28 then decompresses, exerting oppositely directed forces on flange 26 and mounted end 39. The force applied on flange 26 is in the direction of object 100, ensuring that injection end 57 remains in contact with object 100 during withdrawal of tip 21. This ensures that tip 21 is not exposed at any time during withdrawal. The force applied on mounted end 39 is in the direction of syringe 10, pushing housing 24 away from cover 50. As member 28 pushes housing 24 away from cover 50, cover 50 slides within housing 24 back to its safety position at collar end 30, thereby recovering tip 21 back into cover 50, as shown in FIG. 8.

As cover 50 slides back to collar end 30, ring 22 remains near injection end 57 since there is no force on ring 22. When insertion end 51 of cover 50 slides to collar end 30, bodies 38 slide out of collar end 30. Once bodies 38 are outside of collar end 30, they extend radially from stem 16, automatically locking assembly 80 in the safety position illustrated in FIG. 8. Cover 50 only slides within housing 24 again after the user deliberately pushes ring 22 towards collar end 30 to bring bodies 38 flush with cover 50.

As described in the preferred embodiment, the user may want to expose tip 21 for a brief period of time to facilitate exact placement of tip 21 on injection object 100. To temporarily expose tip 21, the user first slides ring 22 towards insertion end 51 to force bodies 38 flush with cover 50. Next the user pulls handles 32 in the direction of mounted end 39 of housing 24 to slide cover 50 towards mounted end 39. Handles 32 slide in slots 56, which guide the handles 32 towards mounted end 39. As cover 50 slides further into housing 24, tip 21 protrudes from hole 58. The user now precisely places tip 21 on injection object 100 and release handles 32 to resume the operation of assembly 80 described above. Other than the differences described, the operation and advantages of this embodiment are the same as the operation and advantages of the preferred embodiment described above.

Figure 11:
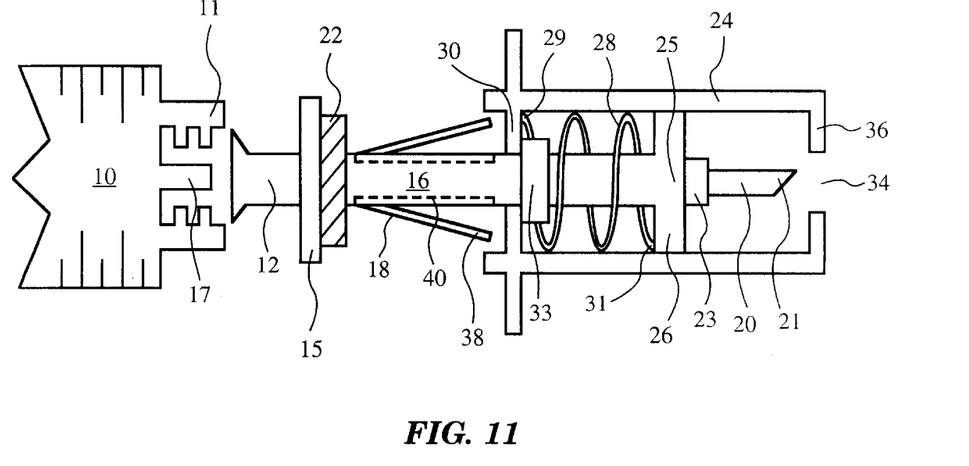
FIG. 11 is a schematic view of another needle guard locked in a position covering a needle.
Figure 12:
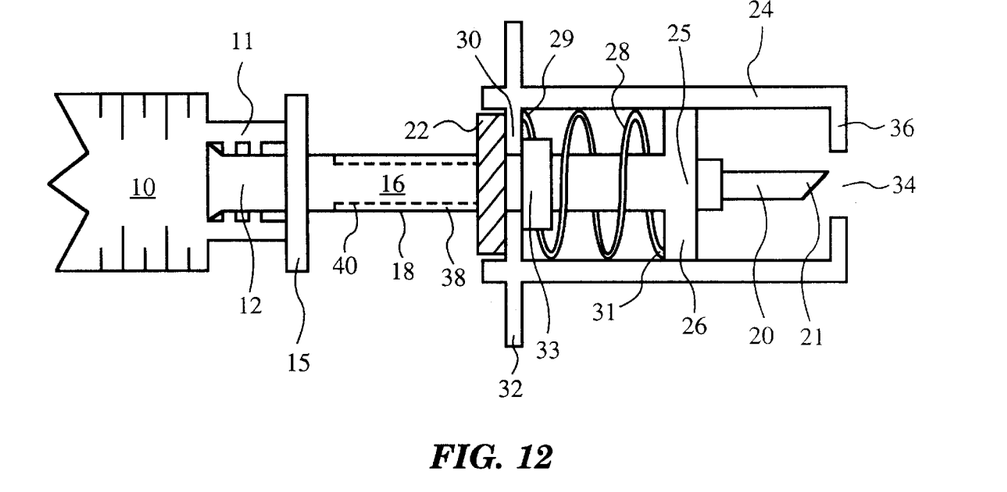
FIG. 12 is a schematic view of the needle guard of FIG. 11 in an unlocked position.
Figure 13:
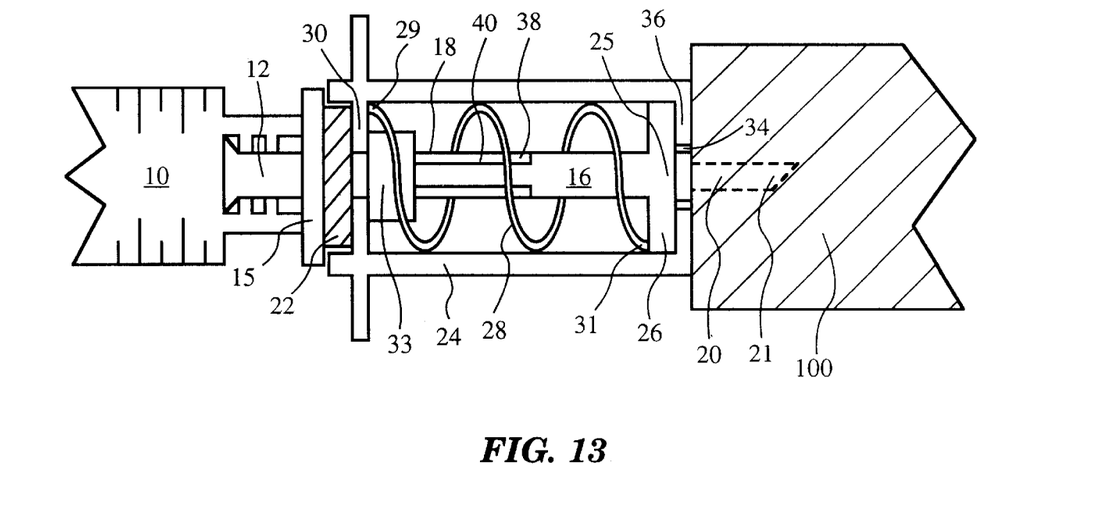
FIG. 13 is a schematic view of the needle guard of FIG. 11 during injection.

A sixth embodiment of the invention is illustrated in FIGS. 11–13. This embodiment differs from the preferred embodiment in that resilient member 28 is placed between collar end 30 and flange 26 instead of being placed between flange 26 and injection end 36. Referring to FIG. 11, member 28 has first end 29 attached to collar end 30 and second end 31 attached to flange 26. Within housing 24, a sleeve 33 is mounted to collar end 30. Sleeve 33 has the same inner diameter as the inner diameter of collar end 30. Sleeve 33 is mounted to collar end 30 with its opening aligned with the opening of collar end 30, such that stem 16 may freely slide through sleeve 33 when it slides into housing 24.

The operation of the sixth embodiment is illustrated in FIGS. 11–13. The operation of the sixth embodiment differs from the operation of the preferred embodiment in the action of resilient member 28 and elastic members 18 during the injection and withdrawal of tip 21. During an injection, stem 16 slides into housing 24, as shown in FIG. 13 and as described in the preferred embodiment above. However, unlike the preferred embodiment where member 28 is compressed, member 28 is now stretched between collar end 30 and flange 26 as distal end 25 of stem 16 advances toward injection end 36 of housing 24. Also as stem 16 advances toward injection end 36, sleeve 33 maintains bodies 38 flush with stem 16 while bodies 38 are inside housing 24. Because sleeve 33 keeps bodies 38 flush with stem 16, bodies 38 do not contact member 28 within housing 24. This ensures that bodies 38 do not interfere with the resilient action of member 28.

During withdrawal of needle 20 from object 100, the user stops pushing syringe 10 towards injection end 36, so that there is no longer a force stretching resilient member 28. Member 28 then contracts, pulling flange 26 and injection end 36 together, thereby recovering needle 20 back into housing 24, as shown in FIG. 11. Except for the differences described, the operation and advantages of this embodiment are the same as the operation and advantages of the preferred embodiment described above.

The assembly of the preferred embodiment of the invention is shown in FIG. 14. First, elastic members 18 are attached onto stem 16 by mounting base 37 around stem 16. At this point, injection end 36 of housing 24 is not yet attached, so that stem 16 can be inserted into housing 24. Stem 16 is inserted until flange 26 contacts collar end 30. Next, resilient member 28 is inserted into housing 24. Then, injection end 36 having hole 34 is attached to housing 24 by screwing or gluing injection end 36 onto housing 24. Next, ring 22 is slid onto stem 16, and placed around base 37 of members 18. Finally, proximal end 12 having stop 15 is attached to stem 16 either by heat, glue, or by screwing it onto stem 16. Needle 20 can be attached to fitting 23 either at the time of manufacture or at the time of use.

Figure 15:
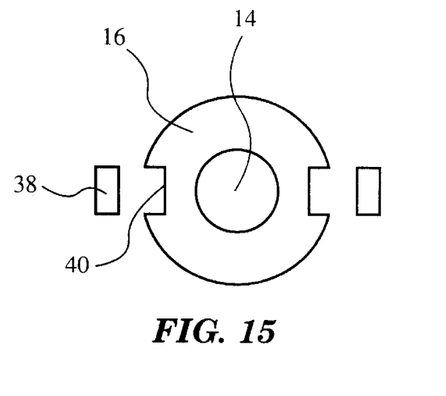
FIG. 15 is a cross-sectional view of the stem and elastic members of FIG. 1.
Figure 16:
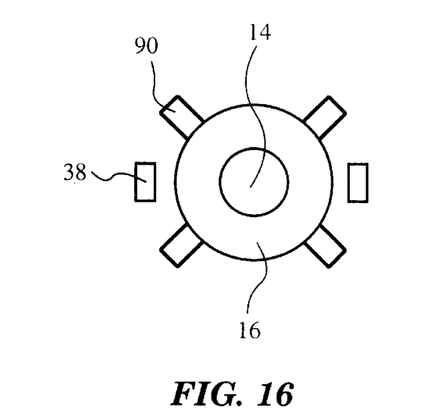
FIG. 16 is a cross-sectional view of an alternate embodiment of the stem and elastic members.

A cross-sectional view of stem 16 is shown in FIG. 15. Stem 16 has two slots 40 into which bodies 38 fit when they are pressed flush with stem 16. An alternate embodiment of stem 16 is shown in FIG. 16. Instead of having two slots 40 on either side, the exterior of stem 16 has four ridges 90 arranged such that each body 38 fits between two ridges 90 when bodies 38 are pressed flush with stem 16. Ridges 90 help to reduce the amount of material required to make stem 16, and therefore make it less expensive to produce.

SUMMARY, RAMIFICATIONS AND SCOPE

While the above description contains many specificities, these should not be construed as limitations on the scope of the invention, but rather as examples of some of the presently preferred embodiments. Many other embodiments are possible. For example, proximal end 12 of stem 16 may be adapted to fit syringe 10 by another method than screwing flanged protrusions 13 into threaded collar 11. Instead proximal end 12 could be force friction fit to syringe 10, or attached by many other methods well known in the art. Also, handles 32 may be attached to housing 24 at a different location than collar end 30 of housing 24 to facilitate finger access to handles 32.

Elastic members 18 are not limited to being leaf springs or L-springs. Further, there may be any number of elastic members 18 attached to stem 16 rather than the two described. Similarly, resilient member 28 need not be the helical spring or collapsible bellows described. Other types of resilient members could successfully be employed. Further, stem 16, housing 24, and cover 50 could have shapes other than the cylindrical shapes described. They could be square, hexagonal, or any other shape that aids the construction and use of needle guard assembly 80.

Accordingly, the scope of the invention should be determined not by the embodiments illustrated, but by the appended claims and their legal equivalents.

I claim:

1. A needle guard for a hypodermic needle, the needle guard comprising:
   a) a stem having a proximal end, a distal end, and an axial opening, wherein the proximal end has a means for attaching the stem to a fluid port, and wherein the distal end has a needle fitting for receiving the needle such that the needle is in fluid communication with the fluid port through the axial opening;
   b) a housing having an injection end and a collar end, wherein the collar end is slidably mounted on the stem to allow the housing to slide on the stem between a first position in which the housing covers the needle and a second position in which the needle partially protrudes from the injection end;
   c) a resilient member lodged between the housing and the stem for biasing the housing toward the first position;
   d) an elastic member having a base attached to the stem and a spring body tending to extend radially from the stem such that the elastic member prevents the housing from sliding from the first position to the second position when the body is radially extended from the stem and such that the elastic member permits the housing to slide from the first position to the second position when the body is flush with the stem; and
   e) a retaining ring slidably fitted around the stem for maintaining the spring body of the elastic member flush with the stem when the retaining ring is located at the distal end and for allowing the spring body to extend radially from the stem when the retaining ring is located at the proximal end.

2. The needle guard of claim 1, further comprising a flanged stop extending radially from the proximal end of the stem for preventing the retaining ring from sliding off the stem.

3. The needle guard of claim 1, wherein the distal end of the stem has a radially extending flange, and wherein the collar end of the housing is mounted on the stem over the flange such that the flange prevents the collar end of the housing from sliding off the distal end of the stem.

4. The needle guard of claim 1, wherein the stem has a slot for receiving the spring body of the elastic member when the spring body is flush with the stem.

5. The needle guard of claim 1, wherein the exterior of the stem has a plurality of ridges, and wherein the body of the elastic member fits between two of the ridges when the body is flush with the stem.

6. The needle guard of claim 1, wherein the elastic member comprises a leaf spring.

7. The needle guard of claim 1, wherein the elastic member comprises an L-spring.

8. The needle guard of claim 1, wherein the resilient member has a first end pressing against a flange of the distal end of the stem and a second end pressing against a wall at the injection end of the housing.

9. The needle guard of claim 1, wherein the resilient member has a first end attached to the collar end of the housing and a second end attached to the distal end of the stem.

10. The needle guard of claim 1, wherein the resilient member comprises a helical spring.

11. The needle guard of claim 1, wherein the resilient member comprises a collapsible bellows.

12. The needle guard of claim 1, further comprising at least one handle attached to the exterior of the housing for facilitating the sliding of the housing toward the proximal end of the stem.

* * * * *